United States Patent [19]

Shiber

[11] Patent Number: 5,002,553
[45] Date of Patent: * Mar. 26, 1991

[54] ATHERECTOMY SYSTEM WITH A CLUTCH

[75] Inventor: Samuel Shiber, Woburn, Mass.

[73] Assignee: Surgical Systems & Instruments, Inc., Mundelen, Ill.

[*] Notice: The portion of the term of this patent subsequent to Nov. 28, 2006 has been disclaimed.

[21] Appl. No.: 323,328

[22] Filed: Mar. 13, 1989

Related U.S. Application Data

[63] Continuation-in-part of Ser. No. 286,509, Dec. 19, 1988, Pat. No. 4,894,051, which is a continuation-in-part of Ser. No. 243,900, Sep. 13, 1988, Pat. No. 4,886,490, which is a continuation-in-part of Ser. No. 78,042, Jul. 27, 1987, Pat. No. 4,819,634, and a continuation-in-part of Ser. No. 205,479, Jun. 13, 1988, Pat. No. 4,883,458, and a continuation-in-part of Ser. No. 225,880, Jul. 29, 1988, Pat. No. 4,842,579, said Ser. No. 78,042, Ser. No. 205,479, and Ser. No. 225,880, each is a continuation-in-part of Ser. No. 18,083, Feb. 24, 1987, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.$^5$ ............................................. A61B 17/20
[52] U.S. Cl. ................................. 606/159; 606/170; 604/22
[58] Field of Search ................ 606/159, 170, 180; 604/22, 95, 264, 267

[56] References Cited

U.S. PATENT DOCUMENTS 4,728,319  3/1988  Masch ................................... 604/22
4,883,458  11/1989  Shiber ................................... 604/22

Primary Examiner—Robert A. Hafer
Assistant Examiner—Kerry Owens
Attorney, Agent, or Firm—Samuel Shiber

[57] ABSTRACT

An atherectomy system for cutting an obstruction in a patient's vessel, comprising a flexible guide-wire insertable into the vessel, a flexible rotary-catheter being rotatably disposed and insertable into the vessel, over the flexible guide-wire, a cutting means for cutting the obstruction, at a distal end of the flexible rotary-catheter, coupling means at the proximal end of the flexible rotary-catheter for engaging a drive means and at least one torque limiting clutch interposed between the drive means and the cutting means, limiting the torque transmitted distally.

3 Claims, 1 Drawing Sheet

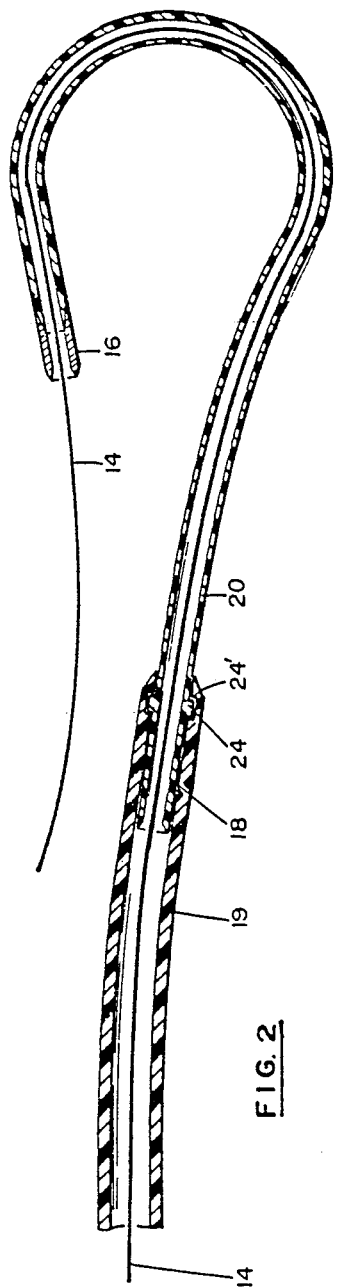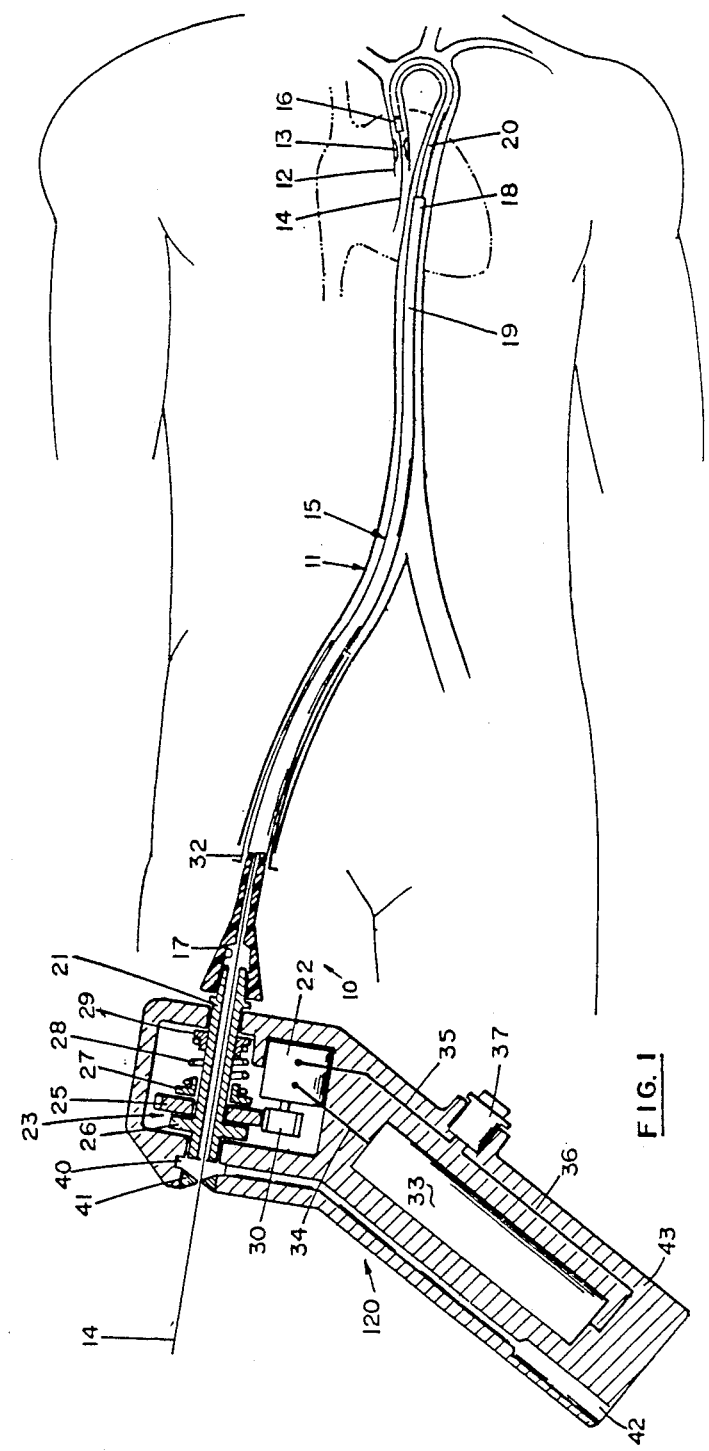

ATHERECTOMY SYSTEM WITH A CLUTCH

CROSS REFERENCE TO OTHER APPLICATIONS

This application is a continuation in part (CIP) of application Ser. No. 07/286,509 filed 12/19/88 (now U.S. Pat. No. 4,894,051) which is a CIP of application Ser. No. 07/243,900 filed 9/13/88 (now U.S. Pat. No. 4,886,490) which is a CIP of three applications, application Ser. No. 07/078,042 filed 7/27/87 (now U.S. Pat. No. 4,819,634) application Ser. No. 07/205,479 filed 6/13/1988 (now U.S. Pat. No. 4,883,458) and application Ser. No. 07/225,880 filed 7/29/88 (now U.S. Pat No. 4,842,579). These three Applications are CIPs of application Ser. No. 07/018,083 filed 2/24/1987, which is a CIP of Application Ser. No. 06/874,546 filed 6/16/1986 (now U.S. Pat. No. 4,732,154) which is a CIP of application Ser. No. 06/609,846 filed 5/14/1984 (abandoned).

All the above applications are being incorporated herein by reference.

BACKGROUND AND SUMMARY OF THE INVENTION

With age a large percentage of the population develops atherosclerotic arterial obstructions resulting in a diminished blood circulation and a variety of related disorders. Presently such obstructions are circumvented by surgically grafting a bypass or they are treated by a catheter equipped with a balloon which is inserted through the arterial system, over a flexible guide-wire, into the obstruction and then inflated to expand the obstruction's lumen (Angioplasty). Some of the problems with Angioplasty are that it injures the arterial wall, it creates a rough lumen and in substantial number of the cases it is ineffective. Further, Angioplasty does not capture and remove the obstruction material out of the arterial system, therefor Angioplasty carries the risk of dislodging obstruction material and allowing it to move down stream creating additional blockages.

An objective of the present invention is to provide an over a guide-wire rotary Atherectomy catheter system, which cuts and removes the obstruction material and which is equipped with torque limiting clutch means to prevent damage to the arterial system. The system may be introduced into the arterial sytem at the groin area, through a sheath to reach a work site in the coronary arteries, which requires a long catheter with an elastic, supple, distal section, a stable diametrical cross section and a torque transmitting ability through the various arteries it is passed through. Meeting these design objectives simultaneously, limits the strength of the distal section (as shown in FIG. 1, the atherectomy system comprises several elongated parts in a nested relationship, and their ends or sections shall be referred to as "distal" meaning the end which goes into the vessel and "proximal" meaning the other end, thus, "distal direction" or "distally" shall indicate a general direction from the proximal end to the distal end, and "proximal direction" or "proximally" shall refer to an opposite direction).

The rotary cutting action which takes place at the distal end of the flexible rotary-catheter requires a certain amount of net torque and rotation. To provide it, the flexible rotary-catheter is driven at its proximal end by a motor, however, due to frictional losses along the length of the flexible rotary-catheter the gross torque that is required at the proximal end is substantially larger than the net torque. To withstand the gross torque the proximal section is strengthened, for example, by increasing its wall thickness or by reinforcing it, and since the proximal section is often disposed in relatively straight arteries, its increased stiffness is acceptable. However, due to various unpredictable and uncontrollable variations that may occur during an individual procedure, such as changes in coefficient of friction between the rotating parts of the system and the stationary parts of the system or of the artery, or changes in the forces inducing the friction which may occur due to misalignment of parts of the system, or a spasm in the artery which may lock the artery onto the rotary catheter, the pattern of torque distribution along the frc may be altered, and it is an important objective of this invention, even under such circumstances, to protect the arteries against injury by either over torquing the artery directly or by over torquing and fracturing the flexible rotary-catheter which may in turn cause injury to the artery.

A numerical example may be helpful: Assuming that the required net and gross torques are 1 inch-ounce and 5 inch-ounce, respectively, and that the ultimate strength of the distal and proximal sections is 3 inch-ounce and 9 inch-ounce, respectively, and further assuming that the motor drive can deliver 7 inch-ounce at stall but because of inherent torque/speed characteristics it will deliver as much as 12 inch-ounce while turning. Thus, it can be seen that if due to an arterial spasm or other cause the blade became locked in the artery, even momentary, the motor may deliver close to 12 inch-ounce of torque to the blade (as previously discussed the frictional losses along the flexible rotary-catheter may occasionally be very small) fracturing the distal section, causing serious complications. If the spasm occurs at a point along the proximal section it can have the same undesirable results. To prevent such complications a first torque limiting clutch rated at 2 inch-ounce is interposed between the distal section and the proximal section and a second torque limiting clutch rated at 6 inch-ounce is interposed between the motor and the drive's output shaft. The first torque limiting clutch enables sufficient working torque to be transmitted to the distal section but prevents destructive torque from reaching it; the second torque limiting clutch does the same for the proximal section.

BRIEF DESCRIPTION OF THE FIGURES

FIG. 1 schematically shows a general view of an atherectomy system according to the present invention, introduced into an arterial system of a patient to cut and remove an obstruction in his heart's artery. The heart outline is shown in phantom lines.

FIG. 2 shows, on a larger scale, a distal section and a part of the proximal section of the flexible rotary-catheter, with a torque limiting clutch interposed between the sections.

DETAILED DESCRIPTION OF THE FIGURES

FIG. 1 schematically shows a general view of the atherectomy system 10 inserted at the groin area of a patient through a sheath 32, through his arterial system 11 into a coronary artery 12 for removing an obstruction 13 therefrom. The system 10 comprises:

A flexible guide-wire 14, insertable into the vessel, a flexible rotary-catheter 15, rotatably disposed and insertable into the vessel, over the flexible guide-wire, a cutting means 16, at a distal end of the flexible rotary-catheter, for cutting the obstruction, coupling means 17 at the proximal end of the flexible rotary-catheter defining a tapered seat for engaging a drive means 120.

A first torque limiting clutch 18, shown also in FIG. 2, is interposed between proximal and distal sections 19 and 20, respectively, of the flexible rotary-catheter. The clutch 18 is formed by fitting the proximal end of section 20 into the distal end of section 19 to establish frictional engagement between the two sections which limits the torque capacity of the clutch to a certain permissible value beyond which the clutch slips, thereby limiting the torque that is transmitted distal to the clutch and protecting the distal section from damage by an occasional transfer of higher torques that may be applied to the proximal end of section 19. A lock-ring 24 formed on section 20 which fits in a corresponding groove 24' defined by section 19, prevents a relative longitudinal displacement between the sections but allows them to rotate relative to one another when the clutch slips.

The drive means 120 has a housing 43 which rotatably supports a hollow shaft 21 through which the guide-wire passes and extends, the distal end of the hollow shaft has a taper for fitting into and engaging with the tapered seat of the coupling means. A motor 22 is coupled to the hollow shaft through a second torque limiting clutch 23. The clutch 23 is made of a gear wheel 25 which is sandwiched between and frictionally engaged with a shoulder 26 formed on the shaft and a pressure plate 27 which is energized against the gear wheel by a compression spring 28 which is supported by a flange 29 which is affixed to the shaft. A pinion 30 which is connected to and driven by the motor 22 is engaged with the gear wheel. The clutch limits the torque delivered to the shaft by the gear wheel 25 by sliding between the shoulder and pressure plate when certain torque is reached, thereby limiting the torque that the drive 120 transmits to the proximal section.

A battery 33 is wired to the motor through a switch 37 by wires 34, 35 and 36. When the switch is depressed it completes an electrical circuit which supplies electrical current to the motor to drive it.

The housing 43 defines an annular cavity 40 and a passage for connecting the hollow shaft to a port 42 for introducing suction or fluids into the flexible rotary-catheter through the hollow shaft. A seal 41 seals the annular cavity while allowing the flexible guide-wire to slidingly extend through the hollow shaft and out of the housing.

The atherectomy system can be manufactured in different diameters and lengths depending on the size and site of artery that it is intended for and on whether the system is to be used percutaneously (that is through the skin) or intra-operatively (that is when the vessel is surgically exposed for inserting the system into the vessel).

While the present invention has been illustrated by one embodiment, it should be understood that various modifications and substitutions may be made without departing from the spirit of the invention or the scope of the claims.

I claim:

1. An atherectomy system for cutting an obstruction in a patient's vessel, comprising in combination:
    a flexible guide-wire insertable into the vessel,
    a flexible rotary-catheter being rotatably disposed and insertable into the vessel, over said flexible guide-wire,
    a cutting means, at a distal end of said flexible rotary-catheter, for cutting said obstruction,
    coupling means at the proximal end of said flexible rotary-catheter for engaging a drive means having a motor,
    wherein at least one torque limiting clutch is interposed between said motor and said cutting means, limiting the torque transmitted distally.

2. An atherectomy system as in claim 1, wherein said torque limiting clutch is interposed between a proximal section of said flexible rotary-catheter to a distsal section of said flexible rotary-catheter.

3. An atherectomy system as in claim 1, wherein said drive means have a hollow shaft through which said guide-wire can pass and extend, a distal end of said hollow shaft engagable with said coupling means,
    a motor coupled to said hollow shaft through torque limiting clutch.

* * * * *